(12) United States Patent
Lee

(10) Patent No.: US 11,484,410 B2
(45) Date of Patent: Nov. 1, 2022

(54) MODULAR AND MULTIFUNCTIONAL APPARATUS FOR ACCELERATED DURABILITY ASSESSMENT OF MEDICAL DEVICES UNDER CYCLIC PRESSURE LOADING

(71) Applicant: Medical Implant Testing Lab, Inc., Irvine, CA (US)

(72) Inventor: Shouyan Lee, Irvine, CA (US)

(*) Notice: Subject to any disclaimer, the term of this patent is extended or adjusted under 35 U.S.C. 154(b) by 348 days.

(21) Appl. No.: 16/785,483

(22) Filed: Feb. 7, 2020

(65) Prior Publication Data

US 2020/0253735 A1 Aug. 13, 2020

Related U.S. Application Data

(60) Provisional application No. 62/802,638, filed on Feb. 7, 2019.

(51) Int. Cl.
*A61F 2/40* (2006.01)
*A61F 2/24* (2006.01)

(52) U.S. Cl.
CPC ...... *A61F 2/2472* (2013.01); *A61F 2240/008* (2013.01)

(58) Field of Classification Search
CPC .......................... A61F 2/2472; A61F 2240/008
See application file for complete search history.

(56) References Cited

U.S. PATENT DOCUMENTS

2014/0076029 A1* 3/2014 Lee ..................... A61F 2/2472
73/37
2017/0227426 A1* 8/2017 Conti ................. G01M 99/007

* cited by examiner

*Primary Examiner* — Jason-Dennis N Stewart
(74) *Attorney, Agent, or Firm* — WPAT Law, P.C.; Anthony King

(57) ABSTRACT

A modular medical testing device at least two driving motor modules, wherein the motors are separately controlled.

10 Claims, 14 Drawing Sheets

MODULAR AND MULTIFUNCTIONAL APPARATUS FOR ACCELERATED DURABILITY ASSESSMENT OF MEDICAL DEVICES UNDER CYCLIC PRESSURE LOADING

CROSS-REFERENCE TO RELATED APPLICATIONS

This application claims priority to, and is a non-provisional patent application of, U.S. Provisional Patent Application No. 62/802,638, filed on Feb. 7, 2019, now pending, which is hereby incorporated by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of all of the prior art of record and any search that the Office deems appropriate.

FIELD OF THE DISCLOSURE

The field of the disclosure is medical devices in general and accelerated durability testing devices specifically.

BACKGROUND OF THE DISCLOSURE

In-vitro durability evaluation of medical devices under cyclic pressure load is typically required from the regulatory bodies. For example, a new prosthetic heart valve design has to withstand 200 million cycles of cyclic pressure loading across the valve at a condition near physiological pressures, as required by ISO 5840. While the normal frequency at which a heart valve functions is around 70 cycles/min, in-vitro evaluation is often much accelerated to shorten time of design evaluation.

In the past, all valve accelerated durability testers are limited to one cycle driving unit for multiple prosthetic valves or recently one unit for one valve. There are two major limits for those tester designs: 1) full valve opening is correlated to the driving power, so is the peak pressure. As a result, in order to maintain a physiological pressure range with full valve opening, the accelerated frequency is limited. For large size valves (29 mm for example), 600 cycles/min is near the maximum testing frequency without high pressure and artifacts. 2) All designs are for single load condition valve durability only and not suitable for other testing such as the frame durability.

There continues to be a need for novel devices and methods of accelerated durability testing of medical prosthetics that may obviate one or more of the above-mentioned limits.

All referenced patents, applications and literatures are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply. The embodiment may seek to satisfy one or more of the above-mentioned desires. Although the present embodiment may obviate one or more of the above-mentioned desires, it should be understood that some aspects of the embodiment might not necessarily obviate them.

BRIEF SUMMARY OF THE DISCLOSURE

Although the features may be described below as acting in certain combinations and even initially claimed as such, one or more features from a combination can in some cases be excised from the combination, and the combination may be directed to a subcombination or variation of a subcombination.

In a general implementation, a prosthesis-testing apparatus is provided where two driving motors are used.

In another aspect combinable with the general implementation, the apparatus can be assembled using at least two modular units that can quickly assemble and disassemble from each other.

In another aspect combinable with the general implementation, the apparatus can be assembled using at least three modular units that can quickly assemble and disassemble from each other.

In another aspect combinable with the general implementation, both driving motors move in a synchronized fashion.

In another aspect combinable with the general implementation, both driving motors move in a reverse synchronized fashion.

In another aspect combinable with the general implementation, both driving motors move in an unsynchronized fashion.

In another aspect combinable with the general implementation, the modular units can be assembled into an accelerated wear tester (AWT) configuration for the testing of an testing valve.

In another aspect combinable with the general implementation, the modular units can be assembled into a stent fatigue tester configuration for the testing of a stent.

In another aspect combinable with the general implementation, the accelerated wear tester configuration can quickly transform into a stent fatigue tester configuration by replacing only the testing module with another type of testing module.

In yet another aspect combinable with the general implementation, the accelerated wear tester configuration can quickly transform again by replacing a driving motor module with a dummy module.

In another aspect combinable with the general implementation, the driving motor module can have a voice coil actuator that drives a piston towards an atrium.

In another aspect combinable with the general implementation, each of the modular units can have chambers or atriums that, upon assembly, are fluidly connected together.

In another aspect combinable with the general implementation, the apparatus has chambers, channels, and atriums that are filled with Newtonian or non-Newtonian fluids.

In another aspect combinable with the general implementation, any one of the modules can be quickly removed and replaced by just a single different type of module thereby changing the function and purpose of the testing apparatus.

In another aspect combinable with the general implementation, the testing apparatus can have two identical motor driving modules detachably connected to a testing module.

In another aspect combinable with the general implementation, the apparatus includes a testing module that can have at least one channel forming a circuitous passageway allowing a testing fluid to flow in a circuitous fashion. In another embodiment, the circuitous passageway is formed entirely within the testing module. In yet another embodiment, this circuitous passageway can be formed by channels in the testing module in combination with channels in the motor driving module.

In another aspect combinable with the general implementation, the testing module does not have a circuitous passageway for fluid; rather, it can contain a single channel to hold a stent. This particular testing module can optionally have a pressurized chamber surrounding the stented channel.

In another aspect combinable with the general implementation, the pressurized chamber can be pressurized by an externally attached pressure source.

In another aspect combinable with the general implementation, the pressurized chamber can be pressed by one of the two driving motor modules such that one driving motor module applies pressure to the chamber while the other driving motor module pressurizes the internal space of the stented channel.

In another aspect combinable with the general implementation, each of the moveable modules can be made of a transparent or semi-transparent material to facilitate viewing of the prosthesis during testing, as well as viewing of various parts of the testing apparatus. Contemplated material can include plastics, acrylics and glass.

In another aspect combinable with the general implementation, observation windows can be provided for direct viewing of the prosthesis during testing.

In another aspect combinable with the general implementation, various sensors and accessories can be connected to the apparatus, such as fluid level sensor, temperature sensor, heating rod, pressure sensor, pressure measurement port, external water reservoir, external water supply pump, circulation port, video recorder, voice recorder, counter, kinetic measurement devices.

Certain features that are described in this specification in the context of separate implementations can also be implemented in combination in a single implementation. Conversely, various features that are described in the context of a single implementation can also be implemented in multiple implementations separately or in any suitable subcombination.

The details of one or more implementations of the subject matter described in this disclosure are set forth in the accompanying drawings and the detailed description below. Other features, aspects, and advantages of the subject matter will become apparent from the description, the drawings, and the claims.

BRIEF DESCRIPTION OF THE DRAWINGS

It should be noted that the drawing figures may be in simplified form and might not be to precise scale. In reference to the disclosure herein, for purposes of convenience and clarity only, directional terms such as top, bottom, left, right, up, down, over, above, below, beneath, rear, front, distal, and proximal are used with respect to the accompanying drawings. Such directional terms should not be construed to limit the scope of the embodiment in any manner.

Figure 1:
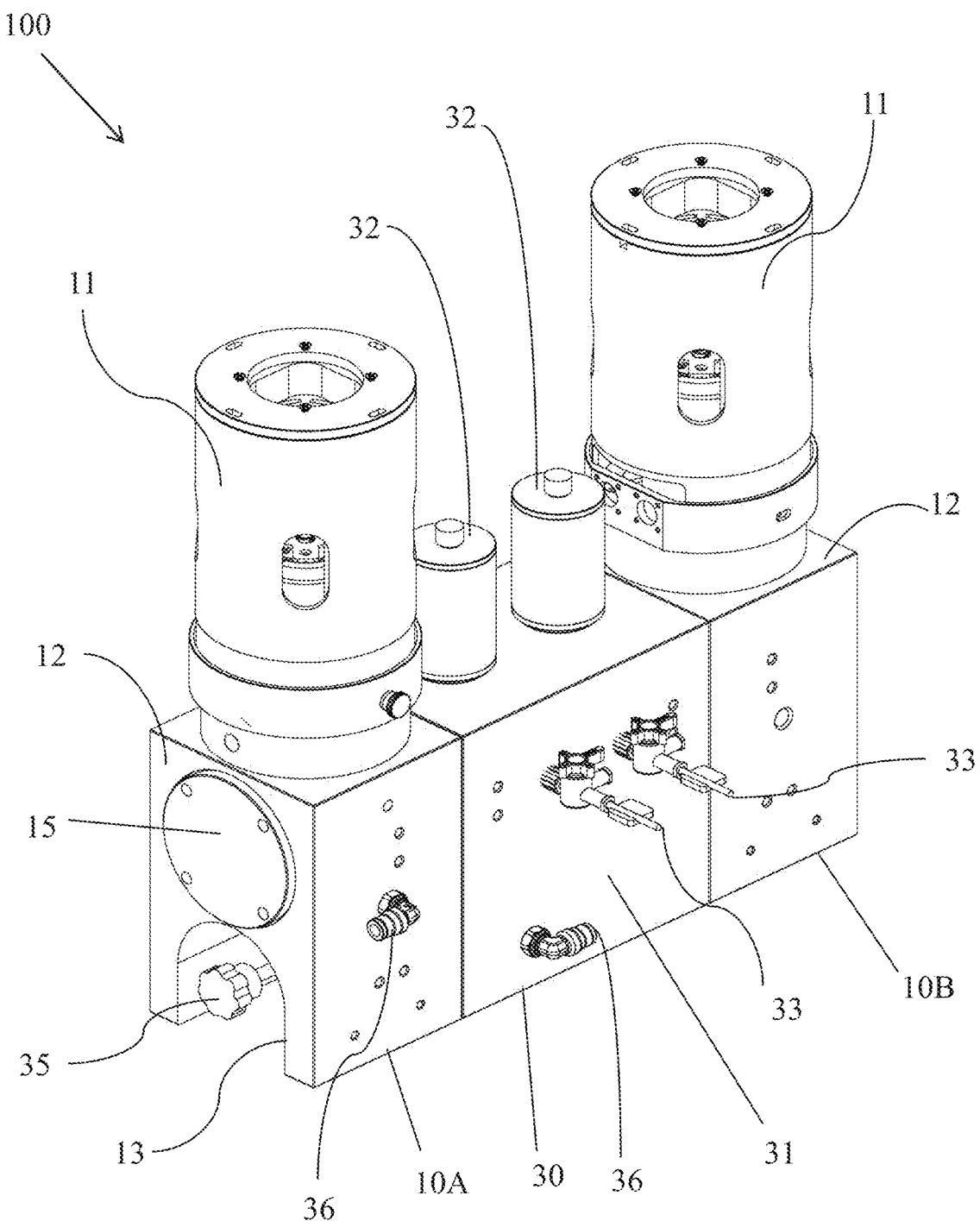
FIG. 1 is a perspective view of one embodiment of an accelerated wear tester (AWT) configuration (with toggle latches removed for easier illustration).

The following call-out list of elements in the drawing can be a useful guide when referencing the elements of the drawing figures:

5 Toggle Latch
10A Driving Motor Module
10B Driving Motor Module
11 Motor Unit
12 Motor Module Body
13 Archway
14 Voice Coil Actuator
15 Transparent View Window
16 Piston
17A Direction of Piston Movement
17B Direction of Piston Movement
18 Atrium
21 First Opening
22A Second Opening
22B Second Opening
22C Second Opening
23A Third Opening
23B Third Opening
23C Third Opening
24 Fourth Opening
30 Valve-Testing Module
31 Valve-Testing Module Body
32 Compliance
33 Pressure Measurement Port
34 Flow Resistance
35 Control Knob
36 Circulation port
37 Heating Rod
38A Channel
38B Channel
38C Channel
38D Channel 50A Stent-Testing Module
50B Stent-Testing Module
51 Stent-Testing Module Body
52 Chamber Space
53 Tube
60 Testing Valve
62 Stent
70 Pressure Source
80 Circuitous Passageway
85 Fluid
86 Medium
90 Dummy Module
91 Compliance
92 Humidity Filter
98 Pressure Port I
99 Pressure Port II
100 Accelerated Wear Tester Configuration
200 Stent Fatigue Tester Configuration
300 Stent Fatigue Tester Configuration
400 Dummy Testing Configuration

DETAILED DESCRIPTION

The different aspects of the various embodiments can now be better understood by turning to the following detailed description of the embodiments, which are presented as illustrated examples of the embodiments as defined in the claims. It is expressly understood that the embodiments as defined by the claims may be broader than the illustrated embodiments described below.

Many alterations and modifications may be made by those having ordinary skill in the art without departing from the spirit and scope of the embodiment. Therefore, it must be understood that the illustrated embodiment has been set forth only for the purposes of example and that it should not be taken as limiting the claims.

Throughout the drawing figures, embodiments having multiple modules are shown. It should be particularly noted that the some of the inventive features can be implemented in a single device without the need for having modular parts. For example, the device shown in FIG. 1 can be a single device instead of three separate modular parts assembled together.

Figure 3:
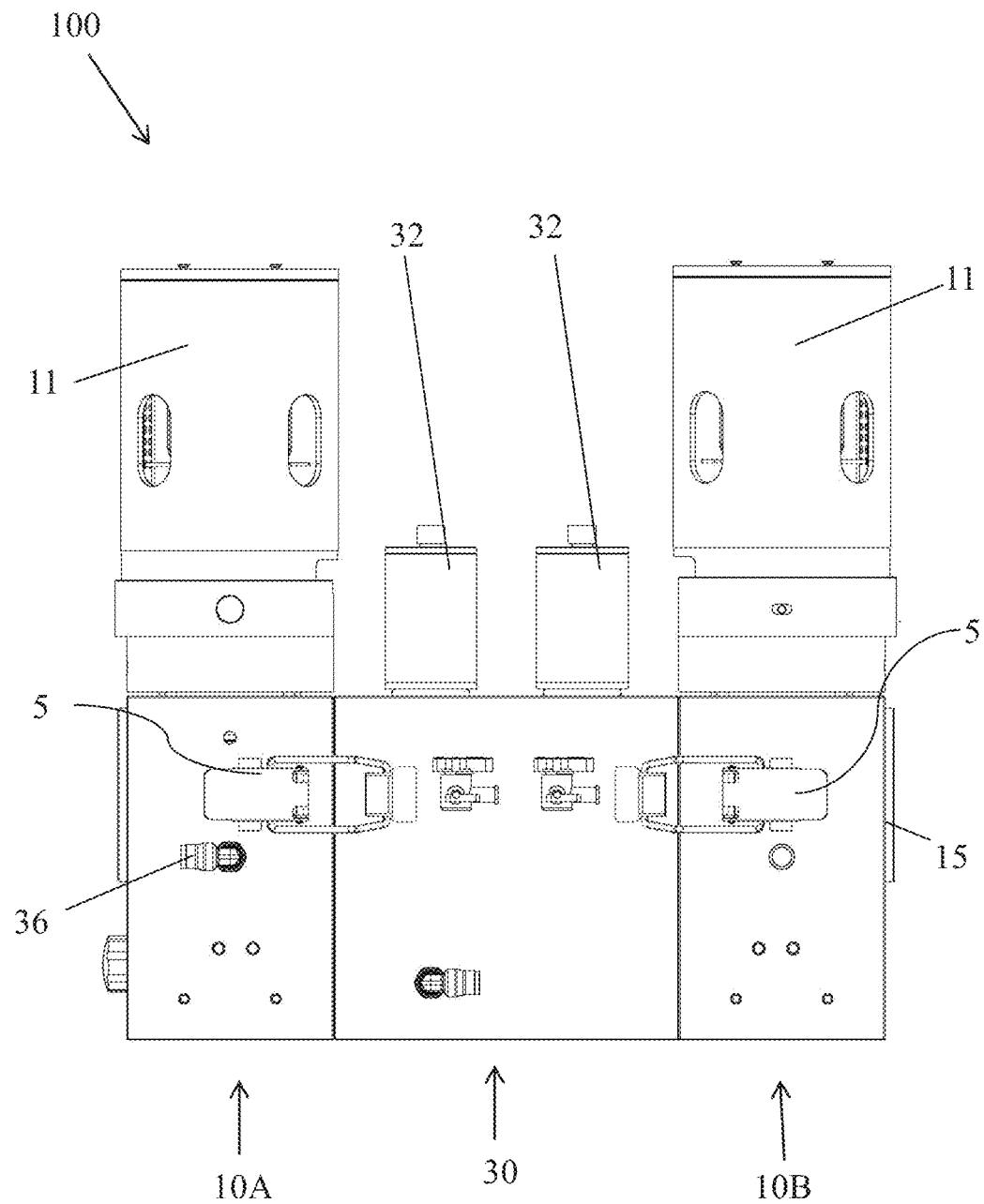
FIG. 3 is a front plan view of the accelerated wear tester (AWT) configuration of FIG. 1 (with toggle latches installed), according to one embodiment.

Referring now to FIG. 1 showing an assembled tester where three separate modular units 10A, 30, 10B can be attached to one another using fasteners such as toggle latches 5 (shown in FIG. 3).

There may be different types of modules each performing a different function and servicing a different purpose. These modules can be quickly latched together to form a specific configuration for a specific test.

In FIGS. 1-6, specific modules are detachably attached together to form an accelerated wear test (AWT) configuration.

Figure 7:
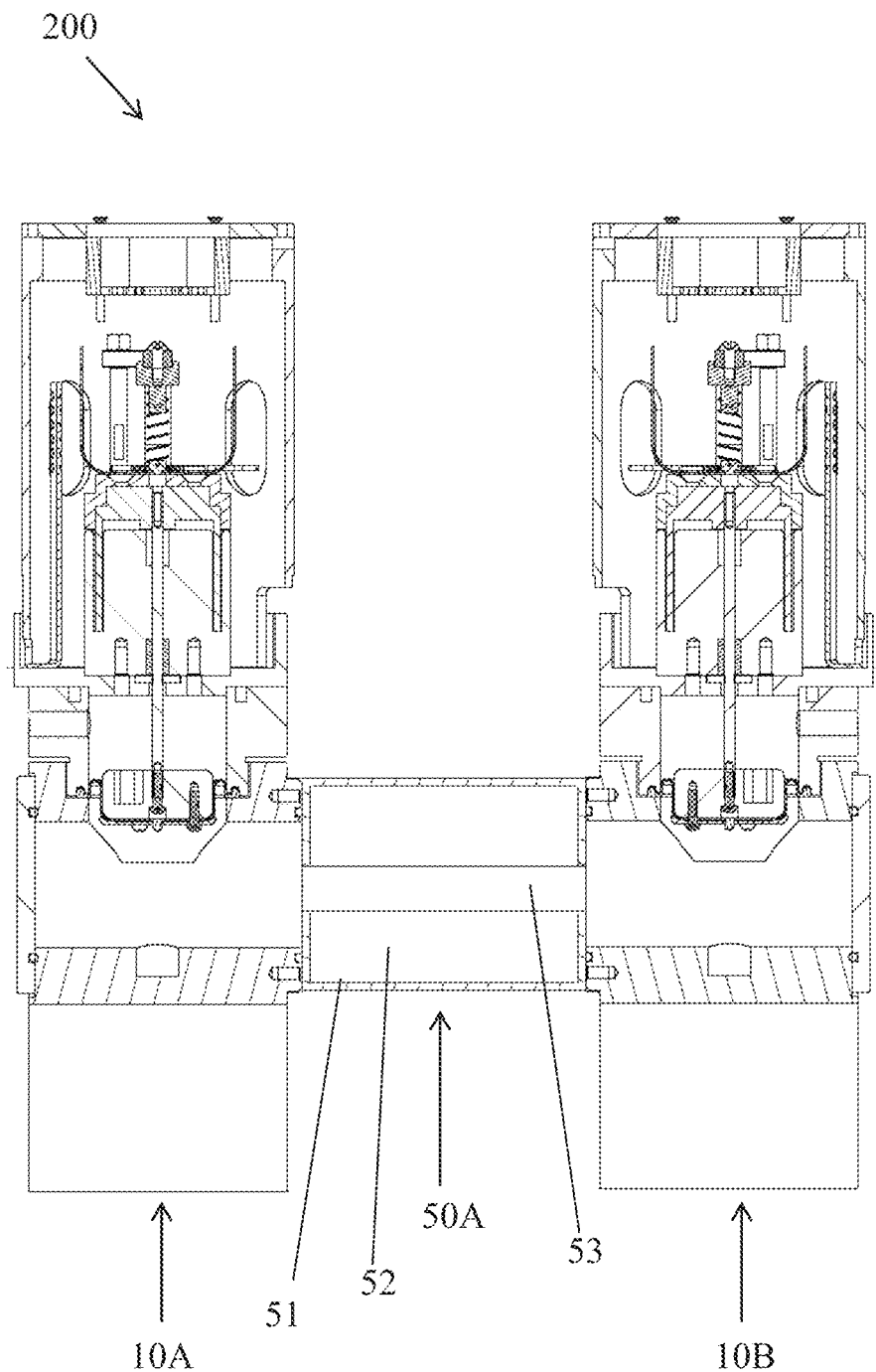
FIG. 7 is a cross-sectional view of one embodiment of a stent fatigue tester configuration where the center module is replaced with a module different from that shown in FIG. 4.
Figure 8:
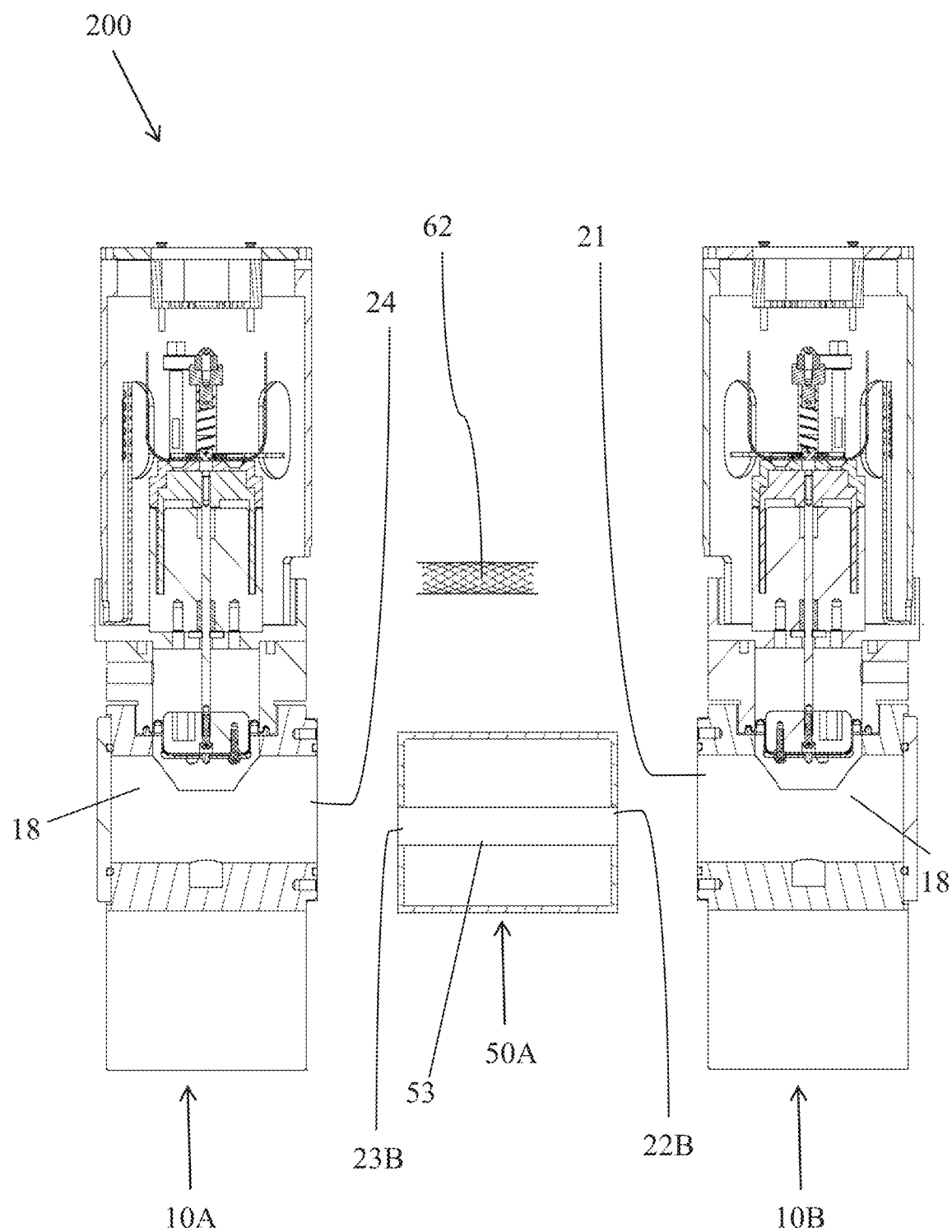
FIG. 8 is a cross-sectional view of the stent fatigue tester configuration of FIG. 7 where the three modules are disassembled from each other, according to one embodiment.
Figure 9:
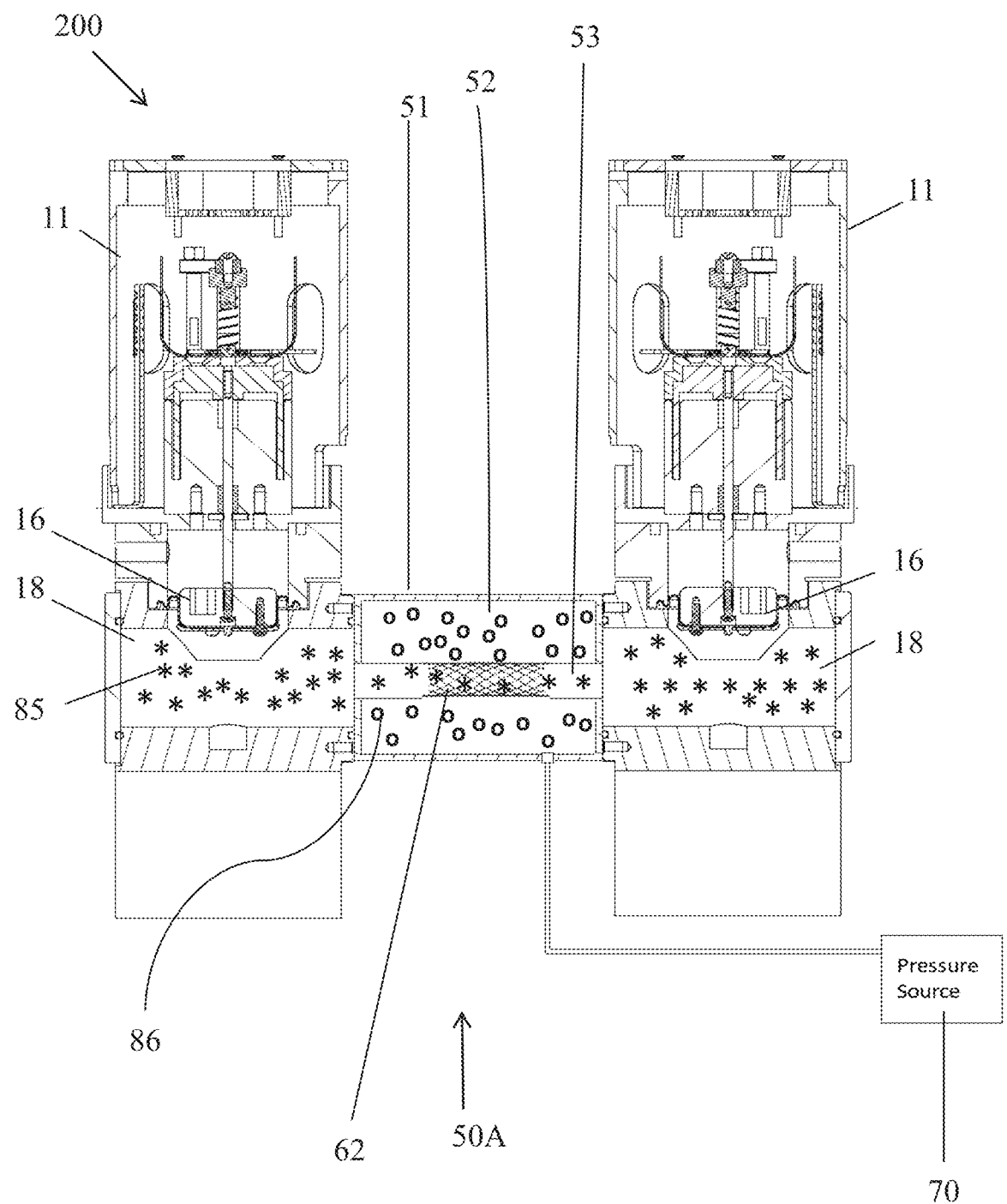
FIG. 9 is a cross-sectional view of the stent fatigue tester configuration of FIG. 7 in operation, according to one embodiment.

In FIGS. 7-9, one module from the AWT configuration can be replaced with another different module to form a stent fatigue testing configuration.

Figure 10:
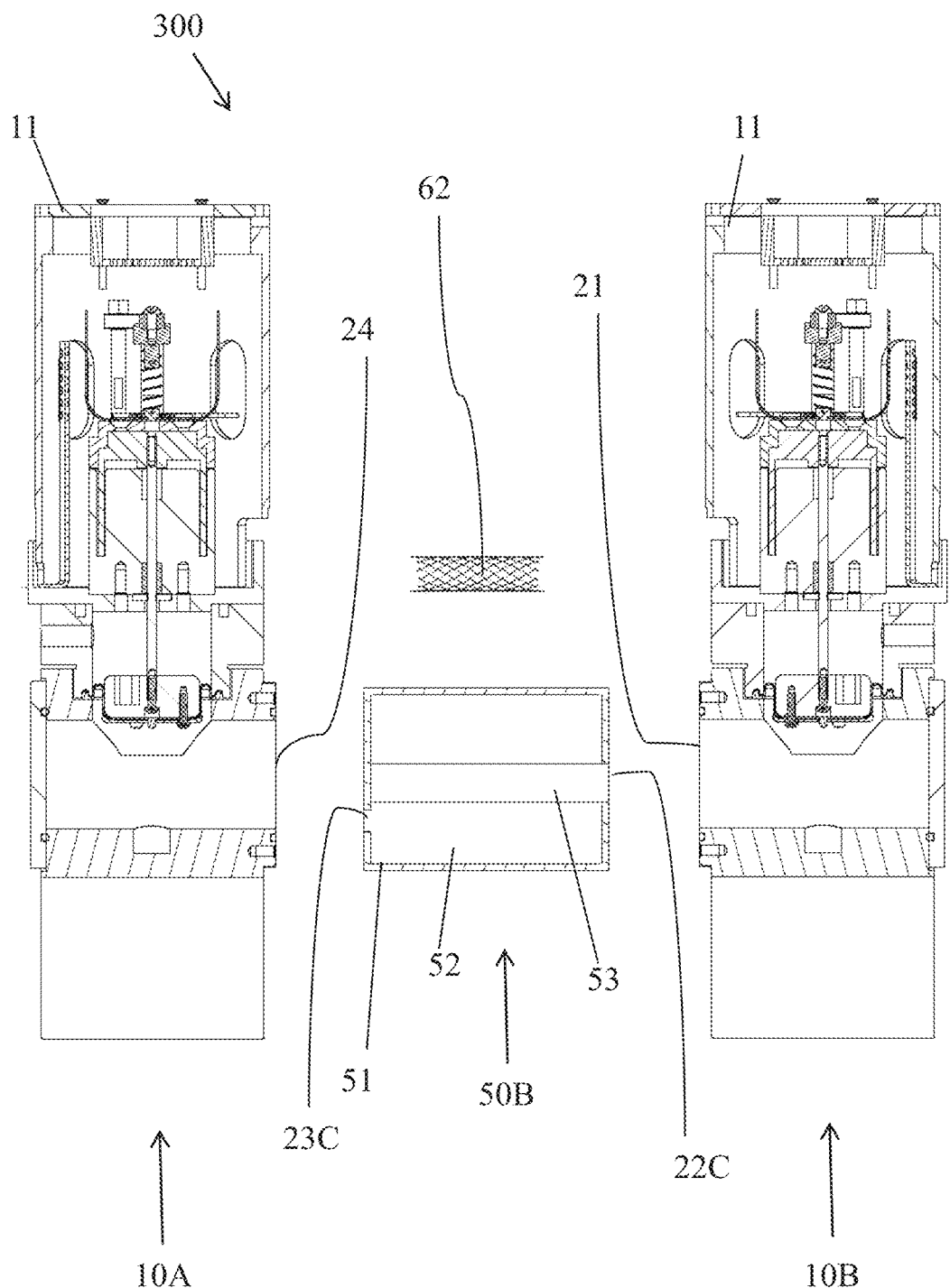
FIG. 10 is a cross-sectional view of another embodiment of the stent fatigue tester where the three modules are disassembled from each other and where the center module is different from that shown in FIGS. 7-9.
Figure 11:
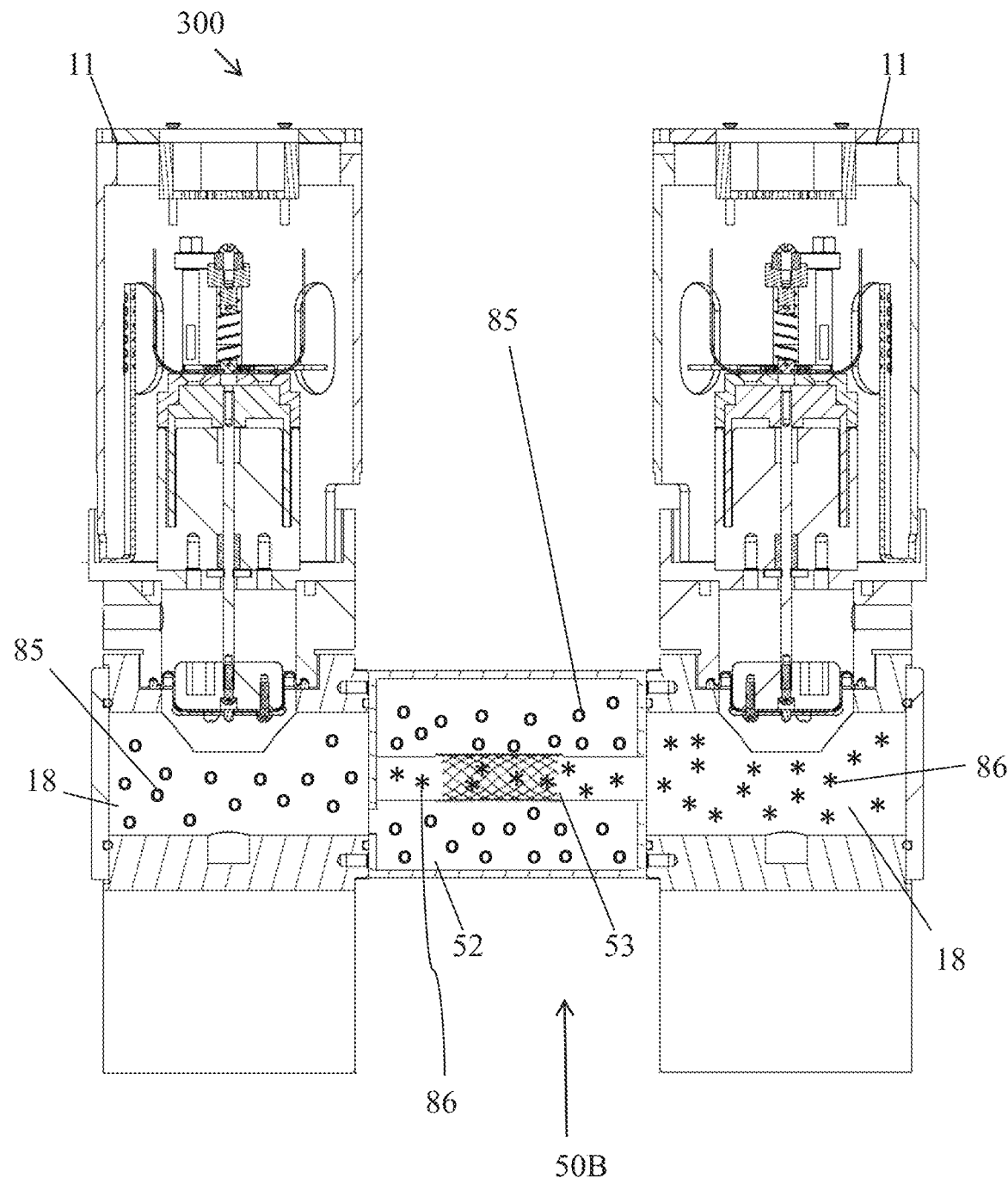
FIG. 11 is a cross-sectional view of the stent fatigue tester configuration of FIG. 10 in operation, according to another embodiment.

In FIGS. 10-11, one module from the stent fatigue testing configuration can be replaced with another different module to form yet another stent fatigue testing configuration.

Figure 12:
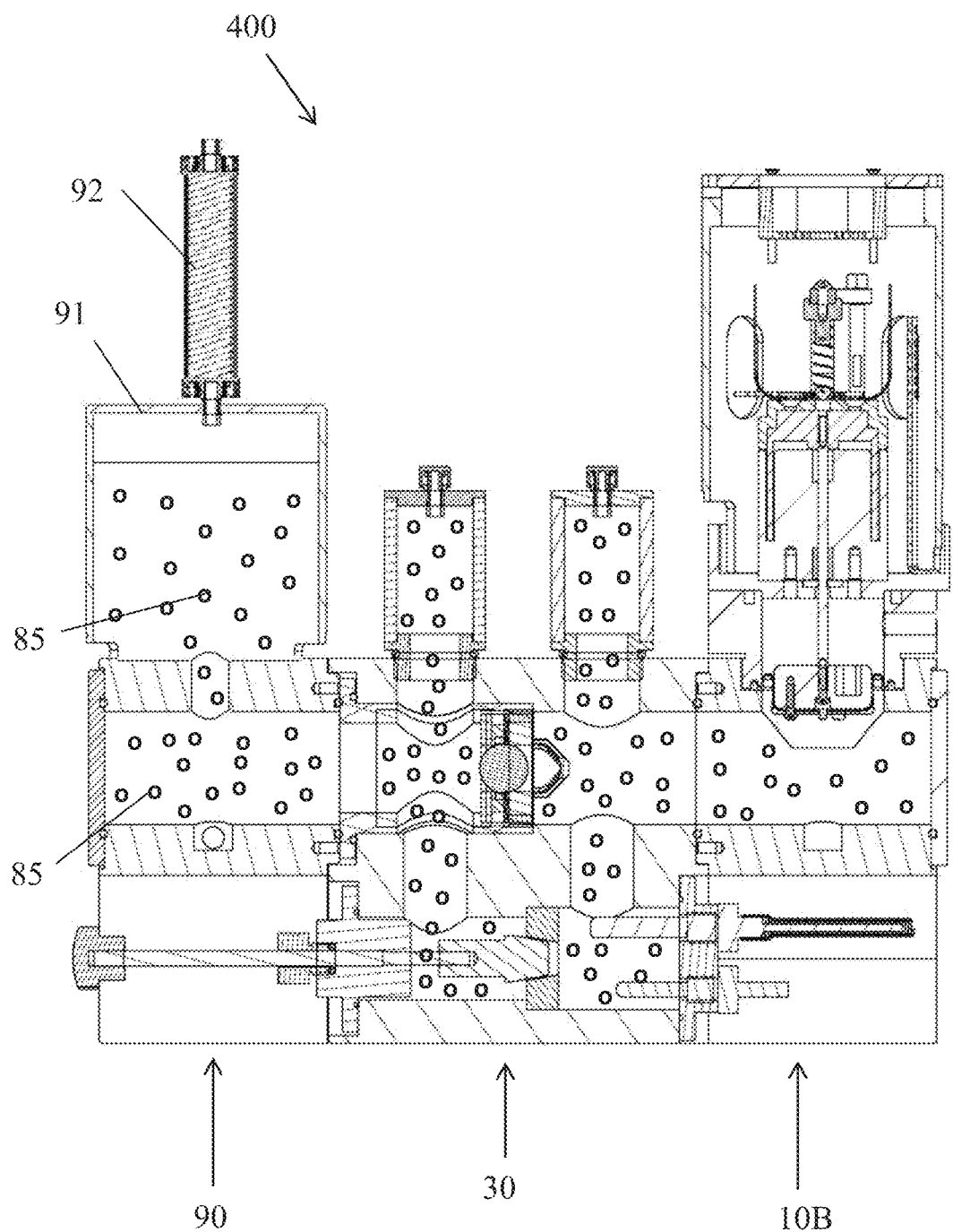
FIG. 12 is a cross-sectional view of a dummy module configuration in operation in accordance to one embodiment of the disclosure.
Figure 13:
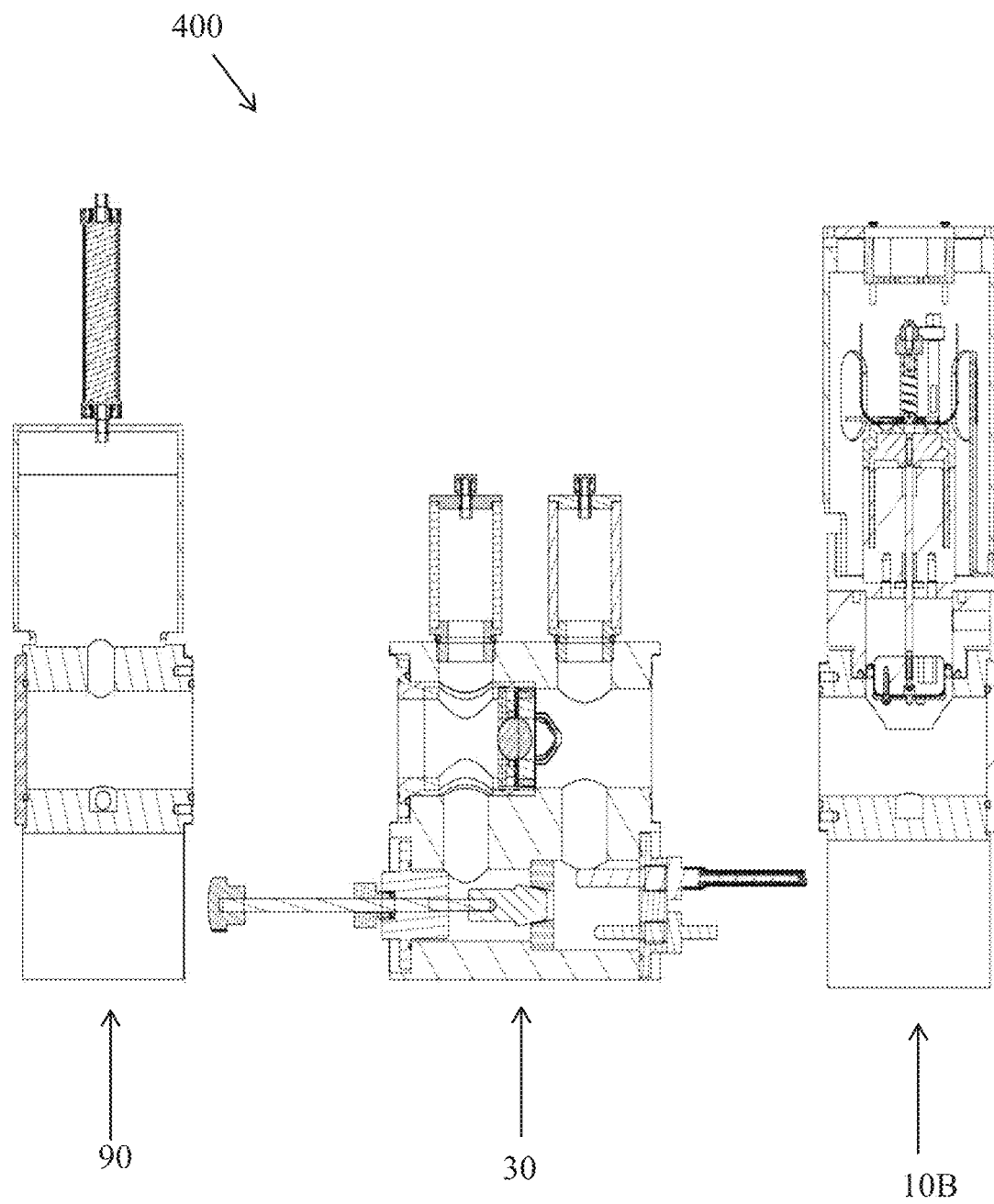
FIG. 13 is a cross-sectional view of a dummy module configuration in accordance to one embodiment of the disclosure, where the three modules are disassembled from each other.

In FIGS. 12-13, one module from the AWT configuration can be replaced with yet another different module to form a dummy testing configuration.

Therefore, the inventor has discovered a unique method to quickly disassemble and assemble a limited number of modules to create testers of different functions and purposes.

In other words, the inventor has discovered a way to create modular pieces that in combination can form different testers for prostheses.

In one embodiment, the novel method allows a user to form a AWT configuration using only three modules, or no more than three modules.

In yet another embodiment, the novel method allows a user to transform a AWT configuration into a stent fatigue tester configuration by replacing only using only one out of the only three modules, or by replacing only one out of no more than three modules.

Referring back again to FIG. 1, an AWT configuration 100 is shown where a valve-testing module 30 is disposed in between two driving motor modules 10A, 10B. The two driving motor modules 10A, 10B can be identical to each other and can be slightly different from one another.

Each driving motor module 10A, 10B can have a motor unit 11 using a voice coil actuator 14, and can be a voice coil actuator-based load generation unit. The detail of the contemplated mechanical design of the voice coil actuator-based generation unit can be similar to the driving motor having a piston and a rolling diaphragm as described in the inventor's U.S. Pat. No. 8,800,348 B2, which is herein incorporated in its entirety.

Notably in FIG. 1 is that each driving motor module 10A, 10B has a motor module body 12 wherein the bottom portion of the motor module body 12 of driving motor module 10A has an archway 13, allowing a user access to the control knob 35 of the flow resistance 34.

Additionally, there can be at least one circulation port 36 disposed on the driving motor module 10A, 10B.

Contemplated embodiment may have a channel 112 for fluid circulation, a flow/Load control valve 113; observation windows 117, 118 to view/record valve motion; and pressure measurement ports 121 measure pressure across the valve 122.

There can be pressure measurement ports 33, positioned on either end of the testing valve (see FIG. 3, 4).

Figure 2:
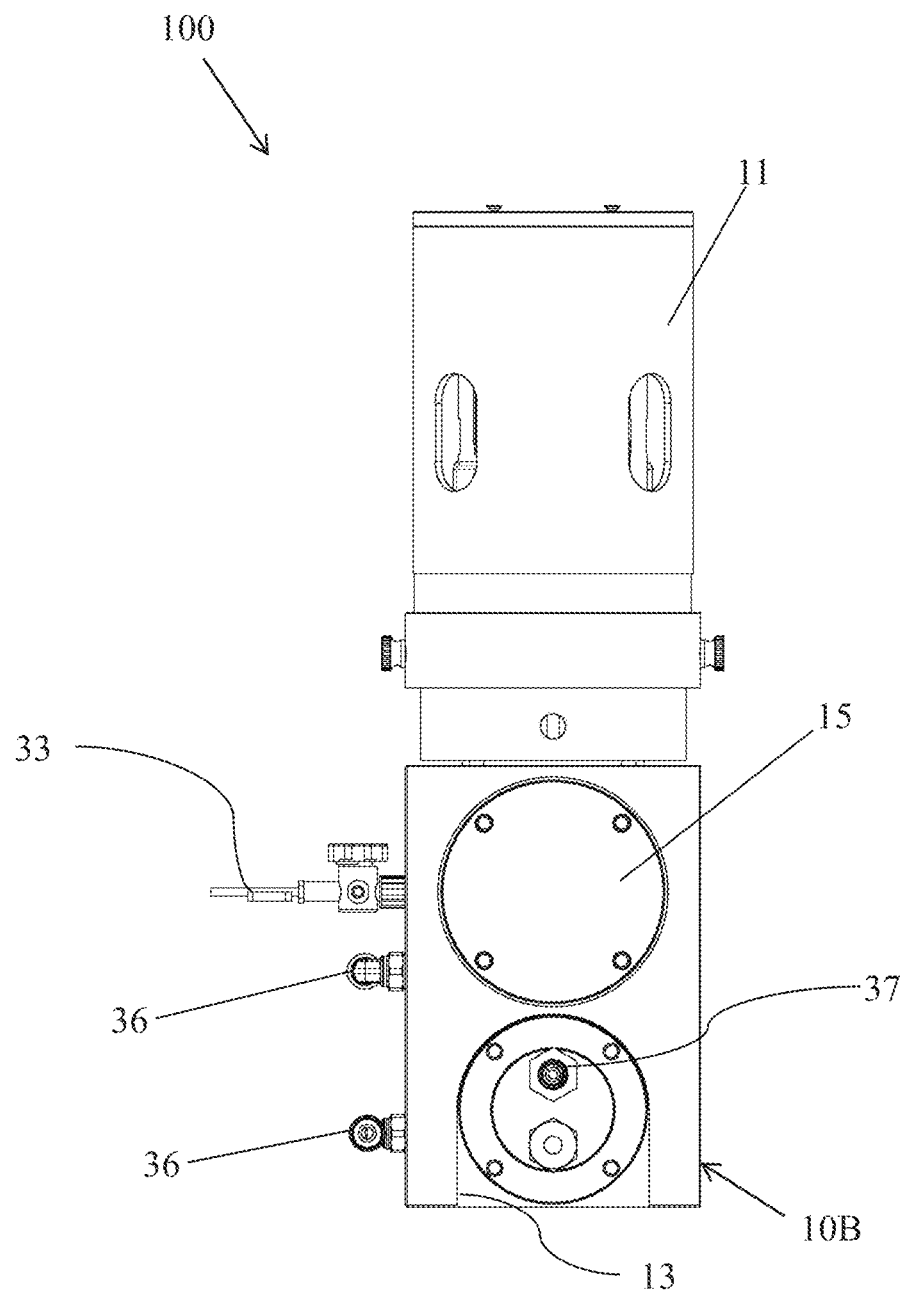
FIG. 2 is right side plan view of the accelerated wear tester (AWT) configuration of FIG. 1, according to one embodiment.

In FIG. 2, the right side view of the AWT configuration can have a transparent view window 15. This transparent view window 15 can or cannot be opened. This view window 15 allows visual monitoring of the testing valve during testing. In one embodiment, this view window does not need to open because placement or replacement of the testing valve is done through opening 22A or opening 22B (FIG. 6) when the modules 10A, 30, 10B are disassembled.

Because there can be provided an archway 13 in motor module body 12 of the driving motor module 10B, a user can access the heating rod 37 without having to first disassemble driving motor module 10B from the valve-testing module 30.

FIG. 3 illustrates the three modules 10A, 30, 10B being fastened together with toggle latches 5, in one particular embodiment. Any of the module-combinations shown in the drawing figures can be fastened together in such fashion. The contemplated toggle latches 5 offer quick and easy assembly and disassembly. Other fastening devices known can be used to achieve similar result of sealingly securing the modules together.

Figure 4:
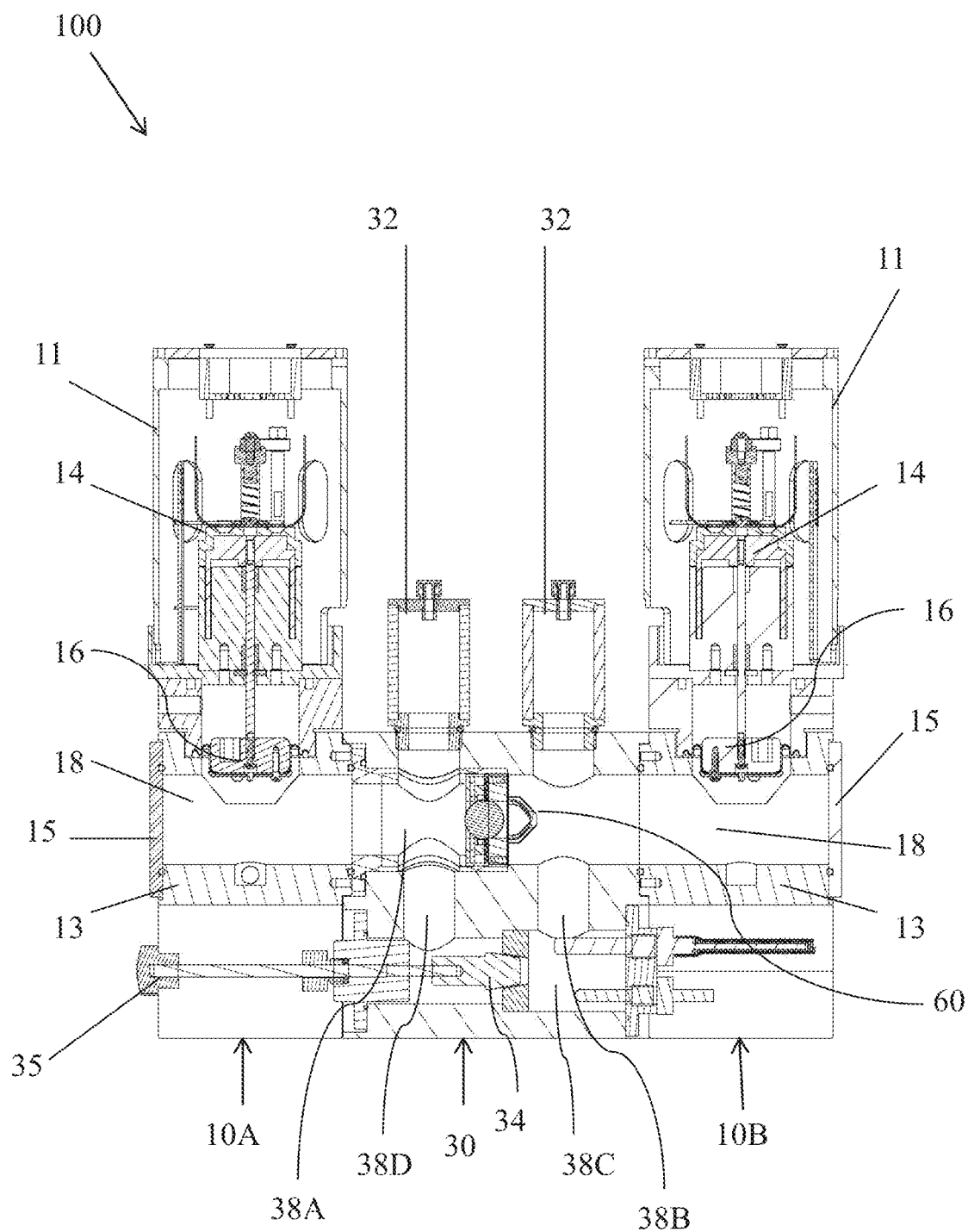
FIG. 4 is a cross-sectional view of the accelerated wear tester (AWT) configuration of FIG. 3, according to one embodiment.

In FIG. 4, additional details of the AWT configuration 100 are shown. Here, driving motor module 10A on the left of the drawing figure can have a voice coil actuator 14 to drive a piston 16 towards an atrium 18 which is disposed in the driving motor body 13.

Similarly, driving motor module 10B on the right of the drawing figure can have a voice coil actuator 14 to drive a piston 16 towards an atrium 18 which is disposed in the driving motor body 13.

The piston 16 is sealingly disposed in the corresponding piston cylinder such that when the piston 16 moves downward, pressure is exerted towards the corresponding atrium 18. Fluid is to stay only on one side of the piston 16, that is, within the atrium 18.

In the assembled state as shown in FIG. 4, the atrium 18 is fluidly connected to channel 38A of the valve-testing module 30. Testing fluid stays within the atrium 18 during operation and does not pass above the piston 16.

In the valve-testing module 30, there can be a channel 38A which can be a straight through-channel connecting one end of the valve-testing module 30 to an opposite end. This means when the three modules 10A, 30, 10B are assembled, the two atriums 18 can be fluidly connected through channel 38A. And when the three modules 10A, 30, 10B are disassembled, the channel 38A is exposed to the ambient environment via openings 22A, 23A (shown in FIG. 6).

In one particular embodiment, the two atriums 18 can be fluidly connected only through channel 38A.

There can be provided seal rings (not shown) or sealants on the interfaces where the modules 10A, 30, 10B make physical and abutting contact together to ensure a seal-tight connection without fluid leakage.

Underneath the atrium 18 of driving motor module 10A is an archway 13 (as indicated in FIG. 1. Through the empty space of the archway 13 is extended the control knob 13 of a flow resistance 34, which is attached to the valve-testing module 30. The purpose of having a flow resistance is well known and the control of which by a control knob 35 is also well known.

In the embodiment shown, the atrium 18 is an empty space enclosed by the walls of the motor module body 12. When the driving motor module 10A, 10B is disassembled from the valve-testing module 30, the atrium 18 would be exposed to the ambient environment because the atrium opens to the ambient environment via opening 21, 24 (shown in FIG. 6). Besides opening 21, 24, the atrium 18 does not have any other openings.

When the modules 10A, 30, 10B are assembled, in one embodiment, the atriums 18 do not fluidly connect to the ambient environment.

A valve-testing module 30 is provided having a testing module body 31 and at least one channel 38A disposed within testing module body 31. The testing module body 31 can be made of a transparent or semi-transparent material to facilitate monitoring of the prosthesis during testing.

The channel 38A can use any known prosthesis holder to hold an testing valve 60 within the channel 38A such that any fluid passing through the channel 38A must pass through the testing valve 60.

The channel 38A can be fluidly connected to channel 38B and 38D, both of which are fluidly connected to channel 38C. The connections of these channels 38A, 38B, 38C, 38D creates a circuitous passageway 80 (shown in FIG. 5), which will be discussed further later.

There can be an optional flow resistance 34 disposed within channel 38C. The purpose and function of a flow resistance 34 is well known; any known type of flow resistance be implemented. Although it is shown in this particular embodiment to have a flow resistance 34 in channel 38C, it is also contemplated to have such flow resistance 34 in channel 38B or channel 38D.

Additionally and optionally, there can be at least one compliance 32 fluidly connected to the channel 38A. Compliance 32 can be attached to any module 10A, 30, 10B or any part of the any module 10A, 30, 10B. In the contemplated embodiment of FIG. 4, there can be two compliances 32 disposed on top of the valve-testing module 30. The two compliances 32 can be used for attenuating high frequency water hammer.

Figure 5:
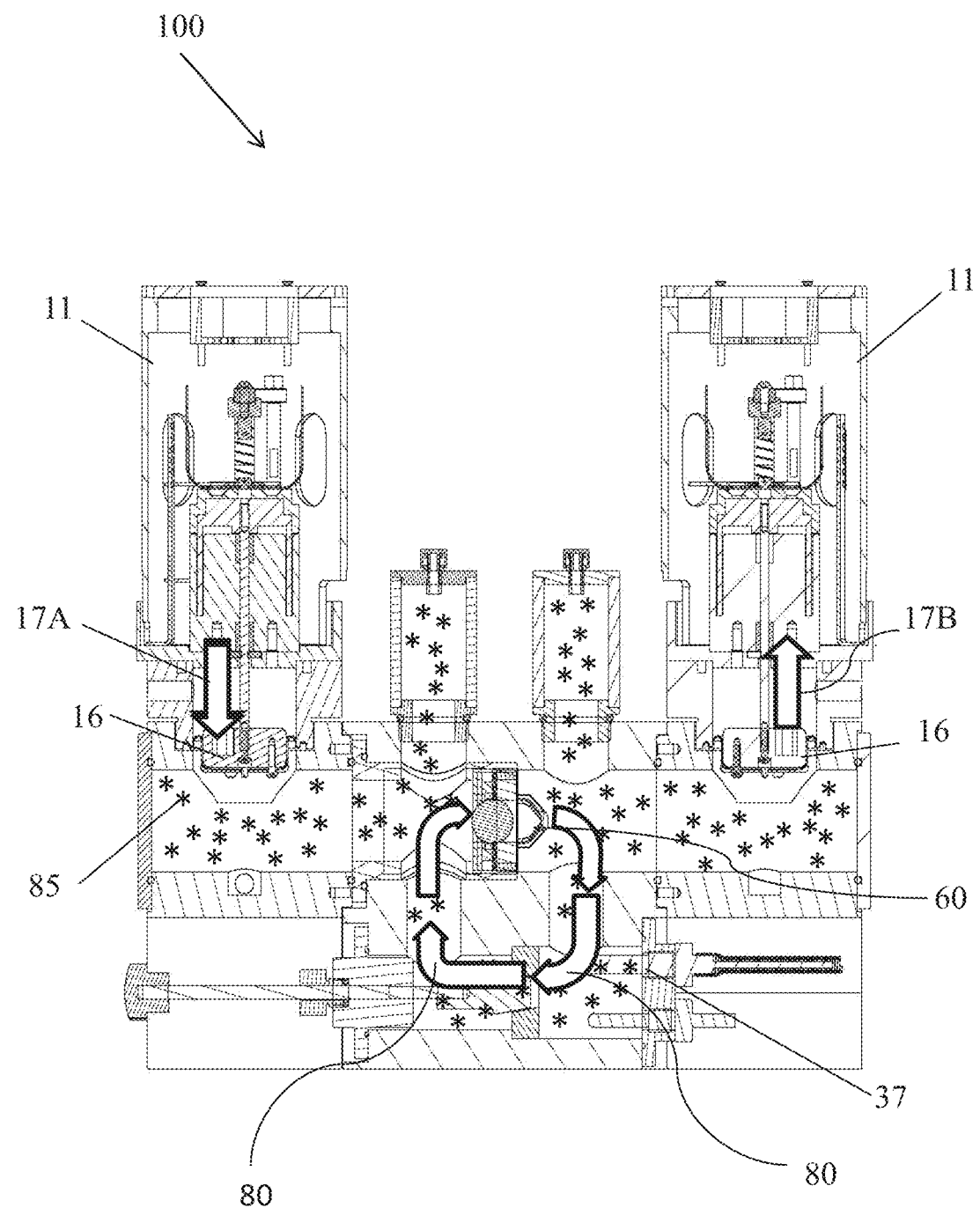
FIG. 5 is a cross-sectional view of the accelerated wear tester (AWT) configuration of FIG. 3 in operation, according to one embodiment.

FIG. 5 illustrates the AWT configuration 100 in operation. Here, the tester is filled with a medium (e.g., gas, liquid, gel) such as a liquid 85 (any known fluid can be used, Newtonian or non-Newtonian). The liquid 85 is shown to fill to the top of the compliance 32, through atriums 18, and channels 38A, 38B, 38C, 38D.

In the AWT configuration, contemplated method including using both motor units 11 each of which are separately controlled from each other, and the frequency, magnitude, and direction of them can be separately controlled by a controller or microprocessor (not shown).

In a contemplated method, the two motor units 11 are to be reversely synchronized in cycle rate. As shown in FIG. 5, when the piston 16 on the left goes down (17A), the piston 16 on the right actively goes up (17B). It can further improve adequate opening and closing of the testing valve 60. By having both pistons 16 move reversely synchronized, a push-pull action can be created.

For example, as shown in FIG. 5, the test valve 60 can open towards the right. During opening phase, the piston 16 on the left moves downwards 17A, pushing the valve 60 to open, while concurrently the piston 16 on the right moves upward 17B, pulling the valve 60 towards open. This push-pull effect produces more effective valve opening kinematics, thus can allow full opening as required by ISO 5840 at higher test frequency.

Since the pushing motion usually plays a larger role during the opening and closing, the separated amplitude control of each channel as shown allows separate tuning of each motor units 11 for opening and closing. As a result, an operator may achieve full opening at higher cycle rate without overloading the testing valve 60 at closing.

In yet another embodiment, the separately controlled motor units 11 allow secondary loading condition to meet other testing requirements. In still yet other embodiments, the modular design can allow other durability testing such as stent durability test (to be discussed below) and possibly other applications.

Figure 6:
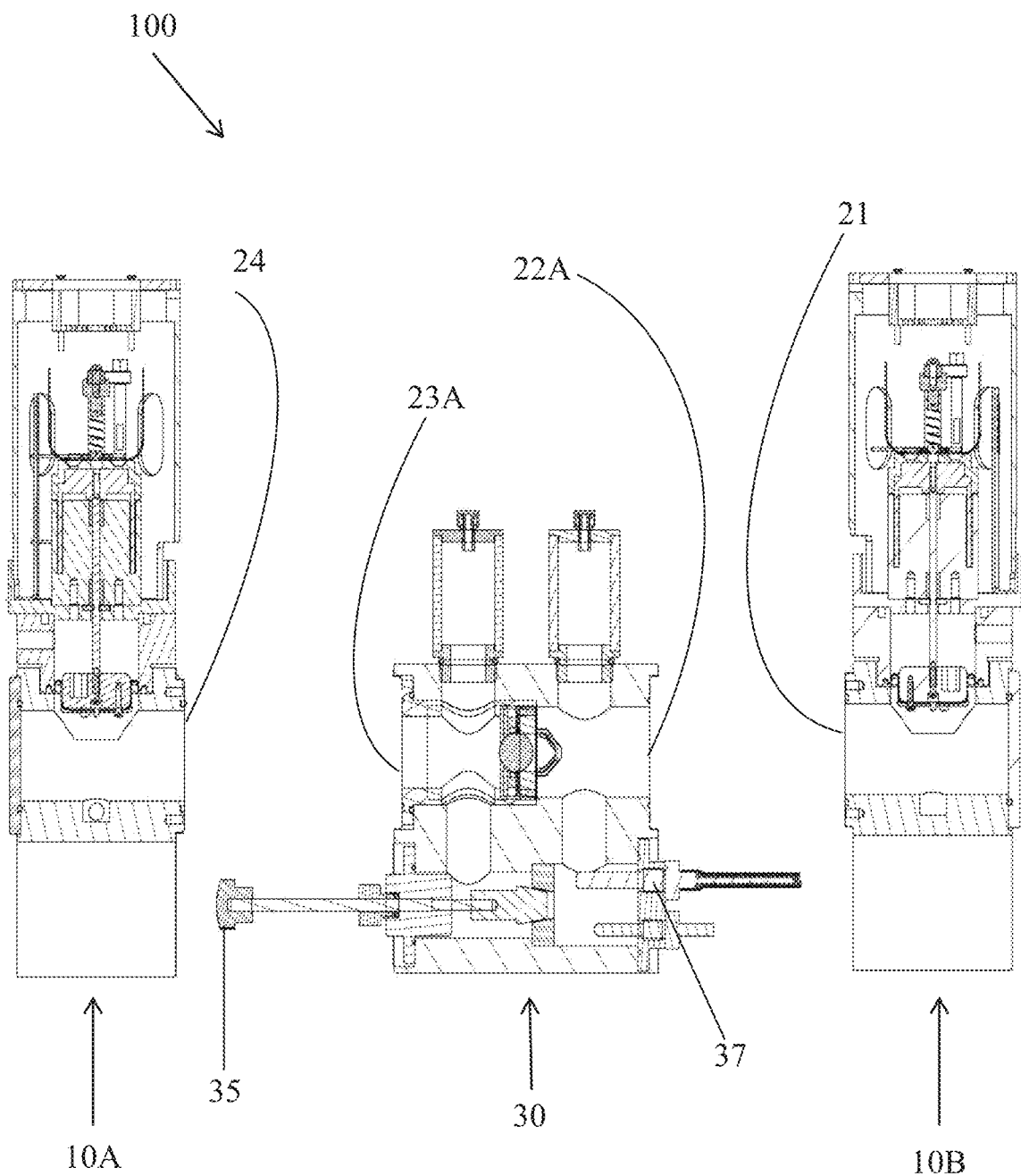
FIG. 6 is a cross-sectional view of the accelerated wear tester (AWT) configuration of FIG. 3 where the three modules are disassembled from each other, according to one embodiment.

FIG. 6 shows the three modules 10A, 30, 10B in a disassembled state. When disassembled, openings 21, 22A, 23A, and 24 are exposed to the ambient environment, as discussed elsewhere in this specification.

FIG. 7 shows a stent fatigue tester configuration 200. Here, driving motor modules 10A, 10B remains the same while the valve-testing module 30 is replaced with a stent-testing module 50A.

The stent-testing module 50A can have a stent-testing module body 51 that can be generally cubic shape. The stent-testing module body 51 can enclose an internal chamber 52 where a tube 53 is disposed.

In all embodiments shown, the tube can be a compliant tube.

In the disclosed stent fatigue tester configuration 200, the three modules 10A, 50A, 10B can be sealingly latched together using toggle latches 5 such as those as shown in FIG. 3.

Referring now to FIG. 8, the three modules 10A, 50A, 10B are disassembled. When disassembled, atriums 18 are exposed to the ambient environment as discussed previously. The tube 53 has openings 22B, 23B disposed at either terminal ends of the tube. When disassembled, the interior space of the tube 53 can be exposed to the ambient environment via openings 22B, 23B. When assembled, the interior space of the tube 53 can be fluidly connected to atriums 18 on both ends.

In one embodiment, atrium 18 on the left can be fluidly connected to atrium 18 on the right only through the tube 53.

A testing stent 62 can be placed into the interior space of the tube 53 via known techniques when the stent-testing module 50A is disassembled from at least one of the driving motor modules 10A, 10B, thereby creating a stented tube.

Referring now to FIG. 9, where the stent fatigue tester configuration 200 of FIGS. 7-8 is now shown in operation. Here, a medium (e.g., gas, liquid, gel) such as a liquid 85 is filled within both atriums 18 as well as the interior space of the tube 53.

The two motor units 11 can be separately controlled to assert a synchronized (in cycle rate) movement where both pistons move in the same direction together (i.e., a pulsatile pressure), for example, when the piston 16 on the left moves up, the piston on the right also moves up.

In another embodiment, the electronic controls can separately control the two motor units for both to actively assert a static pressure.

In yet another embodiment, the electronic controls can separately control the two motor units for reversely synchronized pulsatile pressure.

In still yet another embodiment, the electronic controls can separately control the two motor units for a unsynchronized pulsatile pressure.

There can be a medium (e.g., a gas, a liquid, a gel) disposed within the chamber space 52 surrounding the tube 53. The chamber space 52 does not make fluid connection with the interior of the tube 53. The chamber space also cannot make fluid connection with either atriums 18.

In one embodiment, the chamber space 52 is a closed space.

In another embodiment, the chamber space 52 is fluidly connected to an external pressure source 70 which can be controlled by the microprocessor to exert a desire amount of pressure (e.g., static pressure, pulsatile pressure). The pressure source 70 can be synchronized or reversely synchronized with both motor units 11.

The medium 85 and medium 86 can be the same medium. They are, however, physically separately from each other and do not mix. In another embodiment, the medium 85 and medium 86 cannot be the same medium and they are physically separately from each other and do not mix FIGS. 10 and 11 illustrate another embodiment of stent fatigue tester configuration 300 wherein the stent-testing module 50B is slightly different from the stent-testing module 50A of FIGS. 7-9. Here, the stent-testing module 50B can have a tube 53 that is only open ended at one terminal end. As shown, when disassembled, the interior space of the tube 53 is exposed to the ambient environment only via opening 22C. There is not an opening on the opposite end of opening 22C. When assembled to the driving motor module 10B to the right, the interior space of the tube 53 makes fluid connection with the atrium 18 of driving motor module 10B. As a result, the interior space of the tube 53 can be pressurized by the motor unit 11 of the driving motor module 10B to the right.

On the other hand, when disassembled, the chamber space 52 of the stent-testing module body 51 is exposed to the ambient environment only via opening 23C. When assembled to the driving motor module 10A to the left, opening 23C and opening 24 align. The interior space of the tube 53 thereby makes fluid connection with the atrium 18 of driving motor module 10A to the left. As a result, the interior space of the tube 53 can be pressurized by the motor unit 11 of the driving motor module 10B to the right.

In FIG. 11, medium 85 fills the atrium 18 of the driving motor module 10A to the left as well as the chamber space 52 of the stent-testing module body 51. At the same time, medium 86 fills the atrium 18 of the driving motor module 10B to the right as well as the interior space of the tube 53.

Similarly, the medium 85 and medium 86 can be the same medium. They are, however, physically separately from each other and do not mix. In another embodiment, the medium 85 and medium 86 cannot be the same medium and they are physically separately from each other and do not mix.

By having the capability to separately control the direction, magnitude, and frequency of each motor unit 11, a user can pressurize (e.g., static pressure, pulsatile pressure) medium 85 and medium 86. The two motor units 11 can be synchronized, reversely synchronized, or unsynchronized A static pressure can help to adjust default diameter of the compliant tube 53 which in turn adjust the diameter of the stent 62. Also, the chamber 52 space can be used to apply a static pressure to compensate for variation of the compliance of the stented tube 53.

One of the contemplated advantages of configuration 200, 300 can be that the motors are individually controlled thereby making tuning easier. Tuning can be much easier than an arrangement where many stented tubes are tested by two motor modules.

FIG. 12 illustrates yet another configuration 400 using three modules 90, 30, and 10B assembled together. Module 90 can be a dummy module 90 which can provide zero (rigid) to infinite (open to air) compliance for any testing application that requires only a single driving unit. For example, in such applications, the dummy module 90 would be coupled to the valve-testing module 30 and a single driving motor module 10B.

In the dummy module 90, there can be a compliance 91, a humidity filter 92 which can be opened to the ambient environment. An example of infinite compliance is provided in the embodiment where the humidity filter 92 is open to the ambient environment.

FIG. 13 shows the three modules 90, 30, 10B disassembled. Module 90 has an archway similar to the archway 13 previously discussed in associations with FIGS. 1 and 4.

Here, archway of module 90 serves the same purpose of allowing the control knob 35 to extend therethrough.

Figure 14:
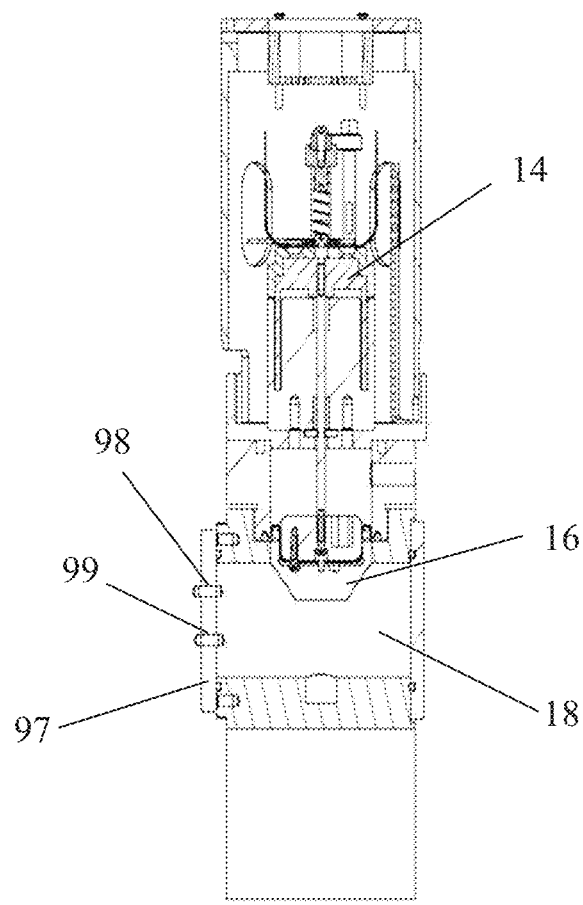
FIG. 14 a sinusoidal pressure generator modified from a driving motor module.

FIG. 14 shows a driving motor module as a sinusoidal pressure generator. Characterization of a dynamic response of a pressure transducer is often challenging, requiring a shockwave tube or a true sinusoidal pressure source of variable frequency. When the atrium 18 is filled with an incompressible fluid (e.g., water) and a sinusoidal current signal is applied to the voice coil actuator 14, the piston 16 will be hardly moving but the force will transfer to the fluid by Pascal's law. Therefore, a true sinusoidal pressure waveform can be obtained with ease.

A pressure port I 98 can be provided on a blocking cover 97 for a pressure transducer to produce dynamic calibration. There can also be a pressure port II 118 on the blocking cover 97 for a second or a reference pressure transducer.

In one embodiment, the atrium must not have any air gap.

In another embodiment, there must not be any air gap within the entire tester system where the testing fluid (incompressible liquid, incompressible gel) is present.

The electronics and control system of the contemplated embodiments can include one central signal generator either through a computer controlled A/D board or standalone signal generation board. Then the signal is split into two (or more) channels for subsequent control of each driving units. The signal can be paralleled or reversed to the driving units. For each channel, the amplitude and position of the motor can be adjusted separately or jointly.

Contemplated embodiments can have servo amplifiers 2-1 and 2-2 for motion control. There can be a displacement sensor (Hall Effect sensor for example) at each motor 3-1, 3-2 so the motor motion can be displacement-controlled or current (force)-controlled with position feedback.

In other contemplated embodiments, pressure transducers and/or other measurement transducers (such as a laser micrometer to monitor stent deflection) can be used with a suitable data acquisition system to tune and monitor the testing parameters.

Thus, specific embodiments and applications of modular and multifunctional apparatus for accelerated durability assessment of medical devices have been disclosed. It should be apparent, however, to those skilled in the art that many more modifications besides those already described are possible without departing from the disclosed concepts herein. The disclosed embodiments, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the embodiments. In addition, where the specification and claims refer to at least one of something selected from the group consisting of A, B, C . . . And N, the text should be interpreted as requiring at least one element from the group which includes N, not A plus N, or B plus N, etc.

What is claimed is:

1. A modular medical prosthesis tester, said tester comprising:
a first driving motor module having a first driving motor module body and a first voice coil actuator to drive a first piston towards a first atrium which is disposed in the first driving motor body;
wherein the first atrium is coupled to a first opening that opens to an ambient environment when the tester is disassembled;
a testing module having a testing module body and at least one channel disposed within the testing module body to hold a medical prosthesis, and the at least one channel is coupled to a second opening that opens to the ambient environment when the tester is disassembled;
wherein the testing module has a third opening that opens to the ambient environment when the tester is disassembled;
a third module having a fourth opening that opens to the ambient environment when the tester is disassembled;
wherein the testing module is detachably attached to the first driving motor module such that the first opening and the second opening are aligned and sealed when the tester is assembled;
wherein the testing module is detachably attached to the third module such that the third opening and the fourth opening are aligned and sealed when the tester is assembled.

2. The tester as recited in claim 1, wherein the third module is a second driving motor module having a second driving motor module body and a second voice coil actuator to drive a second piston towards a second atrium which is disposed in the second driving motor body, and wherein the second atrium is coupled to the fourth opening.

3. The tester as recited in claim 2 further comprising a circuitous passageway, wherein the at least one channel of the testing module forms a part of the circuitous passageway, and wherein the prosthesis is an testing valve.

4. The tester as recited in claim 3 wherein when the first piston moves in one direction, the second piston moves in an opposite direction.

5. The tester as recited in claim 2, wherein the prosthesis is a stent and the testing module body has a chamber space surrounding the at least one channel, and wherein the at least one channel is pressurized by both the first and the second voice coil actuators.

6. The tester as recited in claim 2, wherein the chamber space is pressurized by a pressure source and contains at least one of a gas, a liquid, and a gel.

7. The tester as recited in claim 6, wherein the pressure source is the second voice coil actuator, and wherein the second atrium is fluidly coupled to the chamber space.

8. The tester as recited in claim 6, wherein the pressure source is external to the tester.

9. The tester as recited in claim 6, wherein the chamber space is pressurized by at least one of a static pressure, a pulsatile pressure, a reversely synchronized pulsatile pressure, and a unsynchronized pulsatile pressure.

10. The tester as recited in claim 1, wherein the third module further comprises a compliance that provides zero to infinite compliance, and has a humidity filter attached thereon.

* * * * *